United States Patent
Tanihara

(10) Patent No.: US 8,357,774 B2
(45) Date of Patent: Jan. 22, 2013

(54) POLYPEPTIDE AND PROCESS FOR PRODUCING THE SAME

(75) Inventor: Masao Tanihara, Ikoma (JP)

(73) Assignee: National University Corporation Nara Institute of Science and Technology, Nara (JP)

( * ) Notice: Subject to any disclaimer, the term of this patent is extended or adjusted under 35 U.S.C. 154(b) by 261 days.

(21) Appl. No.: 12/733,621

(22) PCT Filed: Sep. 12, 2008

(86) PCT No.: PCT/JP2008/066568
§ 371 (c)(1),
(2), (4) Date: Mar. 11, 2010

(87) PCT Pub. No.: WO2009/035092
PCT Pub. Date: Mar. 19, 2009

(65) Prior Publication Data
US 2010/0286368 A1    Nov. 11, 2010

(30) Foreign Application Priority Data

Sep. 13, 2007   (JP) ................................ 2007-238437

(51) Int. Cl.
A61K 38/04    (2006.01)
C07K 5/00    (2006.01)
C07K 7/00    (2006.01)
C07K 16/00    (2006.01)
C07K 17/00    (2006.01)
C07K 1/00    (2006.01)

(52) U.S. Cl. .................... 530/327; 530/329; 530/402

(58) Field of Classification Search .................. None
See application file for complete search history.

(56) References Cited

U.S. PATENT DOCUMENTS

| | | | |
|---|---|---|---|
| 7,262,275 B2 * | 8/2007 | Tanihara et al. | 530/356 |
| 7,544,781 B2 * | 6/2009 | Tanihara et al. | 530/356 |
| 8,003,611 B2 * | 8/2011 | Kamitakahara et al. | 514/17.2 |
| 2003/0162941 A1 * | 8/2003 | Tanihara et al. | 530/324 |
| 2007/0207180 A1 | 9/2007 | Tanihara et al. | |
| 2007/0207955 A1 * | 9/2007 | Tanihara et al. | 514/12 |
| 2007/0224251 A1 * | 9/2007 | Tanihara et al. | 424/445 |
| 2008/0009604 A1 * | 1/2008 | Tanihara et al. | 530/341 |
| 2009/0005881 A1 * | 1/2009 | Kamitakahara et al. | 623/23.61 |

FOREIGN PATENT DOCUMENTS

| | | |
|---|---|---|
| EP | 1 288 228 | 3/2003 |
| EP | 1 859 818 | 11/2007 |
| JP | 2003-321500 | 11/2003 |
| JP | 2004-201566 | 7/2004 |
| JP | 2005-58499 | 3/2005 |
| JP | 2005-60314 | 3/2005 |
| JP | 2005-60315 | 3/2005 |
| JP | 2007-223981 | 9/2007 |
| WO | 2006/046569 | 5/2006 |
| WO | 2006/098326 | 9/2006 |

OTHER PUBLICATIONS

Lee et al. Folding Studies of pH-Dependent Collagen Peptides. Chem Biol Drug Des, 2010, vol. 75, pp. 161-168.*
Lee et al.Investigation of pH-Dependent Collagen Triple-Helix Foramtion. 2008, vol. 47, pp. 8429-8432.*
Berg et al. Hydroxylation of (Pro-Pro-Gly)5 and (Pro-Pro-Gly)10 by Prolyl Hydroxylase. Evidence for an Asymemetric Active Site in the Enzyme. Biochemistry, 1977. vol. 16, No. 8, pp. 1615-1621.*
Supplementary European Search Report, dated Jul. 29, 2010, in corresponding European Patent Application No. 08830671.7.
Tanihara M et al. The biodegradability of poly(Pro-Hyp-Gly) synthetic polypeptide and the promotion of a dermal wound epithelialization using a poly(Pro-Hyp-Gly) sponge. J Biomed Mater Res A. Apr. 2008;85(1):133-9.
Kishimoto T et al. Synthesis of poly(Pro-Hyp-Gly)(n) by direct polycondensation of (Pro-Hyp-Gly)(n), where n=1, 5, and 10, and stability of the triple-helical structure. Biopolymers. Oct. 15, 2005;79(3):163-72.
International Preliminary Report on Patentability and Written Opinion of the International Searching Authority mailed Apr. 15, 2010 in International (PCT) Application No. PCT/JP2008/066568.
International Search Report issued Jan. 13, 2009 in International (PCT) Application No. PCT/JP2008/066568.

* cited by examiner

*Primary Examiner* — Marcela M Cordero Garcia
(74) *Attorney, Agent, or Firm* — Wenderoth, Lind & Ponack, L.L.P.

(57) ABSTRACT

The present invention provides a novel polypeptide or polypeptide derivative which has no risk of infection with a pathogen or propagation of a pathogenic factor and of an undesirable side effect, and which is useful as a carrier of various biologically-active substances or apatite, as well as a process for producing the same. More particularly, the present invention provides a polypeptide comprising a peptide unit having an amino acid sequence represented by the formula: -Pro-X-Gly- (wherein X represents Pro or Hyp) and a peptide unit having an amino acid sequence represented by the formula: -Pro-Hyp(O—Y—Z)-Gly- (wherein Y represents a carbonyl group, a saturated or unsaturated hydrocarbon group with or without a carbonyl group, or a saturated or unsaturated hydrocarbon group with or without a carbonyl group, including an aromatic group, and Z represents a carboxyl group), as well as a process for producing the same.

17 Claims, No Drawings

SEQUENCE LISTING

<160> NUMBER OF SEQ ID NOS: 6

<210> SEQ ID NO 1
<211> LENGTH: 14
<212> TYPE: PRT
<213> ORGANISM: Artificial Sequence
<220> FEATURE:
<223> OTHER INFORMATION: Synthetic construct

<400> SEQUENCE: 1

Tyr Arg His Ala Trp Ser Glu Asn Leu Ala Gln Cys Phe Asn
1               5                   10

<210> SEQ ID NO 2
<211> LENGTH: 20
<212> TYPE: PRT
<213> ORGANISM: Artificial Sequence
<220> FEATURE:
<223> OTHER INFORMATION: Synthetic construct -continued

```
<400> SEQUENCE: 2

Lys Ile Pro Lys Ala Ser Ser Val Pro Thr Glu Leu Ser Ala Ile Ser
1               5                   10                  15

Thr Leu Tyr Leu
            20

<210> SEQ ID NO 3
<211> LENGTH: 5
<212> TYPE: PRT
<213> ORGANISM: Artificial Sequence
<220> FEATURE:
<223> OTHER INFORMATION: Synthetic construct

<400> SEQUENCE: 3

Gly Arg Gly Asp Ser
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic construct

<400> SEQUENCE: 4

Val Pro Gly Val Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic construct

<400> SEQUENCE: 5

Pro Pro Gly Pro Pro Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(5)
<223> OTHER INFORMATION: Xaa is hydroxyproline

<400> SEQUENCE: 6

Pro Xaa Gly Pro Xaa Gly
1               5
```

POLYPEPTIDE AND PROCESS FOR PRODUCING THE SAME

This application is a U.S. national stage of International Application No. PCT/JP2008/066568 filed Sep. 12, 2008.

TECHNICAL FIELD

The present invention relates to a novel polypeptide or polypeptide derivative which has no risk of pathogen infection and no undesirable side effect, and which is useful as a carrier of biologically-active substances or apatite, as well as a process for producing the same. More particularly, the present invention relates to a biomaterial or a biocompatible material, a novel polypeptide or polypeptide derivative, which is highly safe and, in particular, which is useful for prosthetics, repair and/or regeneration of a biological tissue, as well as a process for producing the same.

BACKGROUND TECHNOLOGY

Collagen is a fibrous protein which is found in all multi-cellular organisms, and occupies 25% of total proteins as a main component of a skin or a bone in mammals. A typical collagen molecule has a rope-like hyperhelical structure, in which three collagen polypeptide chains form a triple helix structure. Particularly, proline (Pro) and glycine (Gly) are contained in collagen at a large amount, and both amino acid residues are important for formation of a stable triple helix structure.

Examples of a method for using collagen as a biomaterial include a method for transplanting a pig skin tissue itself or a freeze-dried product thereof to a damaged part of the skin such as by burns, a method for using collagen after removing cellular components such as by enzyme treatment, and a method for using collagen obtained by solubilizing collagen by treatment with an acidic solution or an enzyme, and reconstituting this into a desired shape. Non-Patent Document 1 describes a general method of preparation of, and a general method of qualitative analysis of collagen.

There are various proposals about use of collagen.

For example, Patent Document 1 proposes a process for producing a collagen derivative which gives moisture to the skin and smoothes the skin, comprising modifying collagen by esterification of an animal tissue containing collagen with an alcohol, and extracting modified collagen, as well as a cosmetic base using it.

In addition, Patent Document 2 describes a process for producing water-soluble crosslinked collagen which has a high rate of reconstruction to a triple helix structure after heat denaturation, comprising a crosslinking-treating soluble collagen with an alkylene diimidate divalent cross-linker having an imide ester group at both terminals of a methylene chain.

In addition, Patent Document 3 describes a collagen-synthetic polymer matrix which is useful for preparation of a biocompatible implant which is low immunogenic and is used in various medical applications, prepared by reacting collagen with a first synthetic hydrophilic polymer to produce the collagen-synthetic polymer matrix, and reacting the collagen-synthetic polymer matrix with a second synthetic hydrophilic polymer, a biologically-active substance, glycosaminoglycan and a derivative thereof, a chemical cross-linker, an esterifying agent, an amidating agent, an acylating agent, an amino acid, and a polypeptide, etc.

In addition, Patent Document 4 describes a combined product comprising a hydrophilic synthetic polymer covalently-bonded with chemically modified collagen which is substantially in a non-fibrous form at pH 7. The document describes that the combined product is particularly useful in an ophthalmic device and that it is optically transparent and has biocompatibility.

In addition, Patent Document 5 describes a process for producing a membranous collagen substance, comprising grinding and cutting a collagen matrix, centrifuging the ground and cut matrix under a high centrifugal field, homogenizing a precipitate to prepare a paste, casting the paste, and drying the cast paste at 37° C. or lower. The document also describes that the membranous collagen substance is biocompatible and non-inflammatory, and useful for tissue restoration as an artificial implant.

In addition, Patent Document 6 describes highly purified soluble fish scale collagen, and a process for producing the collagen by pepsinating a fish scale itself or after deashing.

In addition, Patent Document 7 describes a process for producing dried granular or powdery soluble collagen, comprising ejecting a collagen solution into a 70-90% ethanol medium through a nozzle to produce a filamentous or membranous product, and drying, and cutting or grinding the product.

In addition, Patent Document 8 describes use of an un-calcined hydroxy-apatite single crystal as a material for restoration of a biological hard tissue such as a bone by attaching the un-calcined hydroxy-apatite single crystal to at least a part of a low antigenic collagen fibril.

In addition, Patent Document 9 describes a method for removing a prion in collagen which is derived from animals or humans, comprising removing a cell and tissue fragment in a collagen solution, and alkalinizing the collagen solution, as well as collagen prepared by this method.

In addition, Non-Patent Document 2 reports that, as to a method of chemical synthesis of a collagen analogue, soluble polyamide having a molecular weight of 16,000-21,000 is obtained by dissolving a p-nitrophenyl ester of Pro-Ser-Gly or a p-nitrophenyl ester of Pro-Ala-Gly in dimethylformamide (DMF), adding thereto triethylamine to allow to stand for 24 hours. Such soluble polyamide is deduced to form a triple-helix structure in the light of circular dichroism spectroscopy, but there is no description about a property of the resulting polymer.

In addition, Non-Patent Document 3 reports a method for preparing polyamide, comprising dissolving in dimethyl sulfoxide a 50-mer peptide containing the Val-Pro-Gly-Val-Gly (SEQ ID NO: 4) sequence derived from elastin, adding 2 equivalents of 1-ethyl-3-(3-dimethylaminopropyl)-carbodiimide, 1 equivalent of 1-hydroxybenzotriazole and 1.6 equivalents of N-methylmorpholine to the solution to allow to stand for 14 days, and dialyzing the solution with a 50,000 molecular weight-cut off dialysis membrane.

In addition, Patent Document 10 discloses that a polypeptide consisting of peptide units represented by the following formulas (1)-(3) can form a collagen tissue.

$$[-(OC-(CH_2)_m-CO)_p-(Pro-Y-Gly)_n-]_a \quad (1)$$

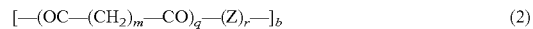

$$[-(OC-(CH_2)_m-CO)_q-(Z)_r-]_b \quad (2)$$

$$[-HN-R-NH-]_c \quad (3)$$

(wherein m represents an integer of 1-18, p and q are the same or different and represent 0 or 1, Y represents Pro or Hyp, n represents an integer of 1-20, Z represents a peptide chain consisting of 1-10 amino acid residues, r represents an integer of 1-20, R represents a linear or branched alkylene group, a ratio between a and b is a/b=100/0-30/70 (molar ratio), and when p=1 and q=0, then c=a, when p=0 and q=1, then c=b, when p=1 and q=1, then c=a+b, and when p=0 and q=0, then c=0).

On the other hand, as described in aforementioned Patent Document 9, it has been said that a causative substance of a sheep tremor disease and bovine spongiform encephalopathy is an infectious protein called a prion, and this infectious protein is one cause of human Creutzfeldt-Jakob disease infection. Non-Patent Document 4 points out that the prion is a protein that is hardly inactivated by a usual sterilization or disinfection method and is infectious across species.

Generally, a medical device, a medicine or a cosmetic often uses collagen derived from cattle or pigs as a raw material. Thus, there is a continued risk of infection (or propagation) with a pathogen (or a pathogenic factor) such as the prion that cannot be removed by the usual sterilization or disinfection method.

In addition, since natural collagen contains various cell adhesive sites, it cannot exert cell selectivity depending upon its application. For example, when collagen is used as a nerve axon-guiding material, an axon cannot extend since a migration rate and a growth rate of a surrounding fibroblast is larger than an extending rate of an axon and a cicatricial tissue is formed. Thus, a mean is necessary, such as covering surroundings of collagen with a material which prevents migration of fibroblast.

On the other hand, it is known that certain ceramics (for example, as bioactive glass, Bioglass (registered trademark), crystallized glass A-W (Cerabone (registered trademark) A-W)) bond with a bone in a living body. This bonding between ceramics and the bone is attributed to formation of a hydroxy-apatite layer on a surface of ceramics in a living body (or in an aqueous solution having an ion concentration close to that of a human body fluid). A bonding mechanism is considered that a silicate ion or a silanol group formed on a surface of the ceramics is first reacted with calcium and phosphoric acid ions in a living body or an aqueous solution to form a core of hydroxy-apatite, and the core grows by incorporation of supersaturated calcium and phosphoric acid ions in the living body or the aqueous solution on the basis of the core.

Patent Document 8 proposes a method for coating a bioactive layer by coating a liquid silica hydrosol or hydrogel on a base such as a metal and ceramics having various shapes such as plate-like, rod-like, fibrous and granular shapes, drying and heating it to bond the silica gel to the base, and immersing the base in an aqueous solution containing calcium and phosphoric acid ions at amounts supersaturated against hydroxy-apatite (mimetic body fluid), thereby, coating a hydroxy-apatite layer on a surface of the base. This document describes that an apatite-coated material can be applied to an artificial bone, and a bio-implantable medical material, device or equipment, etc. However, such the inorganic biomaterial has insufficient biocompatibility such as cell adhesion.

Moreover, an organic-inorganic complex material as a biomaterial is also investigated. For example, Patent Document 12 discloses an organic-inorganic complex biomaterial constituted of hydroxy-apatite of an average fiber length not less than 60 µm and collagen (collagen or a collagenous protein from mammals, birds, fishes, and genetically-engineered collagen, etc.). In addition, this document also describes that the aforementioned complex material can be produced by maintaining a concentration of calcium and phosphoric acid ions in a reaction vessel at a particular level such as by controlling a concentration of a starting material or a flow rate, and pressure-forming the complex prepared. In addition, Non-Patent Document 5 describes a method for complexing collagen and hydroxy-apatite by neutralizing acid-solubilized collagen derived from rat tail tendon in the presence of 0.1 M of $CaCl_2$ and 0.1 M of $NaH_2PO_4$.

However, even in such the complex, there is a risk of pathogen (or pathogenic factor) infection (or propagation) when natural collagen is used as collagen.

In addition, Patent Document 13 discloses a method for producing a complex by contacting an aqueous solution containing calcium and phosphoric acid ions with a base containing sericin to deposit apatite on the base.

In addition, Patent Document 14 discloses a medical treating material in which a particular peptide is immobilized on a base. The medical treating material has the high physiological activity, particularly has strong cell growth promoting action and/or cell adhesion action, and there is described that it is useful as a material or an agent for healing, adhering, reinforcing and/or regenerating a biological tissue.

In addition, Patent Document 15 discloses a peptide having osteogenesis promoting action and an osteogenesis promoting agent containing the peptide as an active agent, which are useful for treatment of fractures, suppression of osteopenia in osteoporosis and a periodontal disease, and prevention of fractures in osteoporosis or rheumatic arthritis.

In addition, Non-Patent Document 6 describes that osteoid calcification is induced over 7 weeks by implanting into a rat crural muscle a material which is prepared by conjugating a peptide having osteogenic action, Lys-Ile-Pro-Lys-Ala-Ser-Ser-Val-Pro-Thr-Glu-Leu-Ser-Ala-Ile-Ser-Thr-Leu-Tyr-Leu-$NH_2$ (SEQ ID NO: 2) to an alginate gel crosslinked with ethylenediamine.

In addition, Non-Patent Document 7 describes that differentiation of a neural stem cell derived from rat hippocampus into a nerve cell is markedly promoted by culturing the neural stem cell on a material prepared by conjugating a peptide having differentiation promotion action for neural stem cells, Tyr-Arg-His-Ala-Trp-Ser-Glu-Asn-Leu-Ala-Gln-Cys-Phe-Asn-$NH_2$ (SEQ ID NO: 1) to the alginate gel.

[Patent Document 1] JP-A 08-027192
[Patent Document 2] JP-A 07-097454
[Patent Document 3] JP-A 08-053548
[Patent Document 4] JP-A 07-278312
[Patent Document 5] JP-A 05-000158
[Patent Document 6] JP-A 05-125100
[Patent Document 7] JP-A 06-228506
[Patent Document 8] JP-A 08-276003
[Patent Document 9] JP-A 08-041425
[Patent Document 10] JP-A 2003-321500
[Patent Document 11] JP-A 5-103829
[Patent Document 12] JP-A 2003-190271
[Patent Document 13] JP-A 2003-154001
[Patent Document 14] JP-A 2006-272002
[Patent Document 15] JP-A 2003-73400
[Non-Patent Document 1] *Methods Enzymol.*, Vol. 82, pp. 33-64 (1982)
[Non-Patent Document 2] *J. Mol. Biol.*, Vol. 63, pp. 85-99 (1972)
[Non-Patent Document 3] *Int. J. Peptide Protein Res.*, Vol. 46, pp. 453-463 (1995)
[Non-Patent Document 4] *Nature Review*, Vol. 2, pp. 118-126 (2001)
[Non-Patent Document 5] *Chem. Mater.*, Vol. 15, pp. 3221-3226 (2003)
[Non-Patent Document 6] *J. Biomed. Master Res.*, Vol. 70A, pp. 115-121 (2004)
[Non-Patent Document 7] *Cell Transplant*, Vol. 14, pp. 665-672 (2005)

DISCLOSURE OF THE INVENTION

Problems to be Solved by the invention

Accordingly, an object of the present invention is to provide a novel polypeptide useful as a carrier of useful substances such as various biologically-active substances, for example, a peptide, or apatite, having no risk of pathogenic infection or pathogenic factor propagation and no possibility of an undesirable side effect, and to provide a process for producing the same.

Means to Solve the Problems

The present inventors studied intensively for solving the problems, and as the result, it was found that a polypeptide (fibrous aggregate) prepared by condensing peptide units having a particular amino acid sequence is useful as a carrier of a biologically-active substance or apatite, which resulted in completion of the present invention.

That is, the present invention provides,

[1] A polypeptide comprising a peptide unit having an amino acid sequence represented by the formula:

-Pro-X-Gly- (1)

(wherein X represents Pro or Hyp)
and a peptide unit having an amino acid sequence represented by the formula:

-Pro-Hyp(O—Y—Z)-Gly- (2)

(wherein Y represents a carbonyl group, a saturated or unsaturated hydrocarbon group with or without a carbonyl group, or a saturated or unsaturated hydrocarbon group with or without a carbonyl group, including an aromatic group, and Z represents a carboxyl group);
[2] The polypeptide according to [1], wherein Y is one or more groups selected from the group consisting of —(C=O)—(CH$_2$)$_n$— (wherein n represents an integer of 0 or 1-18); —(C=O)—(CH$_2$)$_n$—(CH=CH)$_m$—(CH$_2$)$_k$— (wherein n and k represent independently an integer of 0 or 1-18, and m represents an integer of 1-18); and —(C=O)—(CH$_2$)$_n$—(C$_6$H$_4$)—(CH$_2$)$_k$— (wherein n and k represent independently an integer of 0 or 1-18, and C$_6$H$_4$ represents a phenylene group);
[3] The polypeptide according to [1], wherein a ratio between said polypeptide unit (1) and said polypeptide unit (2) ((1)/(2)) is 99.9/0.1-1/99 in terms of a molar ratio;
[4] The polypeptide according to any one of [1] to [3], which exhibits positive Cotton effect at a wavelength of 220-230 nm and negative Cotton effect at a wavelength of 195-205 nm in circular dichroism spectroscopy;
[5] The polypeptide according to [4], wherein at least a part of the polypeptide forms a triple helix structure;
[6] The polypeptide according to any one of [1] to [5], which has a peak in a molecular weight range of 5×10$^3$-5×10$^6$;
The polypeptide according to any one of [1] to [6], which can form a collagen tissue;
[8] A polypeptide derivative, in which one or more substances selected from the group consisting of a peptide, a protein, a polypeptide, a nucleic acid, a sugar, a polysaccharide, a lipid, a polyethylene glycol derivative, an antimicrobial agent, apatite and a complex thereof are conjugated to the polypeptide as defined in any one of [1] to [7];
[9] A polypeptide derivative, in which the substances as defined in [8] are conjugated to a Hyp, residue of the polypeptide as defined in any one of [1] to [7] via a dicaboxylic acid linker of the polypeptide;

[10] A polypeptide derivative, in which apatite is carried by the polypeptide or polypeptide derivative as defined in any one of [1] to [9];
[11] A process for producing the polypeptide as defined in [1], comprising reacting a compound represented by the formula:

HO—Y—Z (3)

or an anhydride thereof,
(wherein Y represents a, carbonyl group, a saturated or unsaturated hydrocarbon group with or without a carbonyl group, or a saturated or unsaturated hydrocarbon group with or without a carbonyl group, including an aromatic group, and Z represents a carboxyl group), with a polypeptide prepared by condensing a peptide unit having an amino acid sequence represented by the formula:

H-(Pro-Pro-Gly)$_o$-OH (1a)

(wherein o represents an integer of 1 or more), and a peptide unit having an amino acid sequence represented by the formula:

H(-Pro-Hyp-Gly-)$_p$-OH (2a)

(wherein p represents an integer of 1 or more);
[12] A process for producing a polypeptide derivative, further comprising reacting one or more substances selected from the group consisting of a peptide, a protein, a polypeptide, a nucleic acid, a sugar, a polysaccharide, a lipid, a polyethylene glycol derivative, an antibacterial agent, apatite and a complex thereof with the polypeptide in the process as defined in [11];
[13] A process for producing a polypeptide derivative, further comprising conjugating one or more of said substances to a Hyp residue of the polypeptide via a carboxylic acid linker of the polypeptide in the process as defined in [12];
[14] A process for producing a polypeptide derivative carrying apatite, comprising contacting the polypeptide or polypeptide derivative as defined in any one of [1] to [9] with an aqueous solution containing calcium and phosphoric acid ions to deposit apatite on the polypeptide or polypeptide derivative;
[15] The process according to [14], wherein said apatite is hydroxy-apatite;
[16] A polypeptide derivative carrying apatite, prepared by the process as defined in [14] or [15]; and
[17] A polypeptide derivative comprising a peptide unit having an amino acid sequence represented by the formula:

-Pro-Hyp-Gly- (1b)

and a peptide unit having an amino acid sequence represented by the formula:

-Pro-Hyp(O—CO—(CH$_2$)$_2$—CO-AA)-Gly- (2b)

(wherein AA represents OH or Tyr-Arg-His-Ala-Trp-Ser-Glu-Asn-Leu-Ala-Gln-Cys-Phe-Asn-NH$_2$ (SEQ ID NO: 1)).

Effect of the Invention

The novel polypeptide or polypeptide derivative of the present invention has no risk of pathogenic infection or a side effect, and has high safety and cytophilicity. In addition, the polypeptide (particularly a fibrous aggregate of the polypeptide) which binds to, or carries a useful substance such as various biologically-active substances, for example, a peptide, or apatite can form a complex with the polypeptide or apatite which is useful for prosthetics, repair and/or regeneration of the biological tissue. Such the polypeptide derivative or the complex is suitable as a repair or regenerating material for a biological tissue or as a biomaterial.

BEST MODE FOR CARRYING OUT THE INVENTION

In the first aspect, the present invention provides a novel polypeptide.

The polypeptide of the present invention comprises a peptide unit having an amino acid sequence represented by the formula:

-Pro-X-Gly- (1)

(wherein X represents Pro or Hyp), and a peptide unit having an amino acid sequence represented by the formula:

-Pro-Hyp(O—Y—Z)-Gly- (2)

(wherein Y represents a carbonyl group, a saturated or unsaturated hydrocarbon group with or without a carbonyl group, or a saturated or unsaturated hydrocarbon group with or without a carbonyl group, including an aromatic group, and Z represents a carboxyl group).

The ratio between the peptide units (1) and (2) constituting the polypeptide is preferably (1)/(2)=99.9/0.1-1/99, more preferably 99.5/0.5-2/98, and most preferably 99/1-5/95 in terms of a molar ratio. It is not preferable when the ratio (1)/(2) exceeds 99.9/0.1, since an amount of a substance conjugated via a linker, which will be illustrated below, is decreased and an objective effect is not adequately exerted. On other hand, it is not also preferable when the ratio is below 1/99, since it becomes difficult to form a fibrous aggregate structure.

Y in the formula represents a dicarboxylic acid linker group for conjugating the useful substance to the polypeptide, and Z is a terminal of the dicarboxylic acid linker and represents a carboxyl group. In the case where Y is —(C=O)—(CH$_2$)$_k$—, n represent an integer of preferably 0 or 1-18, more preferably 1-15, and most preferably 2-12. In addition, in the case where Y is —(C=O)—(CH$_2$)$_n$—(CH=CH)$_m$—(CH$_2$)$_k$—, n and k independently represent an integer of preferably 0 or 1-18, more preferably 1-15, and most preferably 2-12, and m represents an integer of preferably 0 or 1-18, more preferably 1-12, and most preferably 1-8. Furthermore, in the case where Y is —(C=O)—(CH$_2$)$_n$—(C$_6$H$_4$)—(CH$_2$)$_k$—, n and k independently represent an integer of preferably 0 or 1-18, more preferably 0-12, and most preferably 0-8, and C$_6$H$_4$ represents a phenylene group.

Such the dicarboxylic acid linker may be formed by adding dicarboxylic anhydride to a polypeptide chain. That is, in the case where Y is —(C=O)—(CH$_2$)$_n$—, oxalic anhydride, malonic anhydride, succinic anhydride, 4-carboxybutyric anhydride, 5-carboxyvaleric anhydride, 6-carboxycaproic anhydride, 7-carboxyheptanoic anhydride, 8-carboxycaprylic anhydride, or 9-carboxypelargonic anhydride, etc., can be reacted with a hydroxyl group of a hydroxyproline residue of the polypeptide chain, thereby, adding the anhydride thereto. In the case where Y is —(C=O)—(CH$_2$)$_n$—(CH=CH)$_m$—(CH$_2$)$_k$—, maleic anhydride, pent-2-en diacid anhydride, hexa-3-en diacid anhydride, citraconic anhydride, etc., can be reacted with a hydroxyl group of a hydroxy proline residue of the polypeptide chain, thereby, adding the anhydride thereto. In the case where Y is —(C=O)—(CH$_2$)$_n$—(C$_6$H$_4$)—(CH$_2$)$_k$—, phthalic anhydride, etc., can be reacted with a hydroxyl group of a hydroxy proline residue of the polypeptide chain, thereby, adding the anhydride thereto.

At least a part of the polypeptide of the present invention forms a triple helix structure in an aqueous solution, a mixture of alcohol and water, or a buffer such as a phosphate buffer, etc., at 4-60° C. The polypeptide of the present invention exhibits positive Cotton effect at a wavelength of 220-230 nm and negative Cotton effect at a wavelength of 195-205 nm in circular dichroism spectroscopy.

In addition, the polypeptide of the present invention has a degree of polymerization exhibiting a peak in a range of a molecular weight of preferably $5 \times 10^3$-$5 \times 10^6$, more preferably $1 \times 10^4$-$3 \times 10^6$, and most preferably $2 \times 10^4$-$1 \times 10^6$.

In the second aspect, the present invention provides a process for producing the aforementioned polypeptide.

The polypeptide of the present invention can be produced by reacting the compound represented by the formula:

HO—Y—Z (3)

or an anhydride thereof, (wherein Y represents a carbonyl group, a saturated or unsaturated hydrocarbon group with or without a carbonyl group, or a saturated or unsaturated hydrocarbon group with or without a carbonyl group, including an aromatic group, and Z represents a carboxyl group), with a polypeptide prepared by condensing a peptide unit or a peptide fragment having an amino acid sequence represented by the formula:

H-(-Pro-Pro-Gly-)$_o$-OH (1a)

(wherein o represents an integer of 1 or more), and a peptide unit or a peptide fragment having an amino acid sequence represented by the formula:

H-(Pro-Hyp-Gly)$_p$-OH (2a)

(wherein p represents an integer of 1 or more).

Examples of the compound (3) which can be used for producing the polypeptide of the present invention include oxalic acid, malonic acid, succinic acid, 4-carboxybutyric acid, 5-carboxyvaleric acid, 6-carboxycaproic acid, 7-carboxyheptanoic acid, 8-carboxycaprylic acid, 9-carboxypelargonic acid, maleic acid, pent-2-enoic diacid, hexa-3-enoic diacid, citraconic acid, phthalic acid, etc. But, malonic acid, succinic acid, 4-carboxybutyric acid, maleic acid and phthalic acid are preferable.

Particularly, the polypeptide of the present invention can be produced by dissolving a peptide unit such as H-Pro-Pro-Gly-OH or a peptide fragment such as H-Pro-Pro-Gly-Pro-Pro-Gly-OH (SEQ ID NO: 5) which is a dehydrated condensate of the peptide unit (1a) and a peptide unit such as H-Pro-Hyp-Gly-OH or a peptide fragment such as H-Pro-Hyp-Gly-Pro-Hyp-Gly-OH (SEQ ID NO: 6) which is a dehydrated condensate of the peptide unit (2a) in a suitable buffer, adding thereto a condensation additive such as 1-hydroxybenzotriazole, adding a dehydration-condensation reagent such as 1-ethyl-3-(3-dimethylaminopropyl)-carbodiimide hydrochloride to the solution under cooling, and continuing stirring to obtain the reaction solution, and dialyzing the resulting reaction solution against a suitable buffer.

The reaction of these ingredients can be conducted in a solvent which can dissolve or suspend (partly or entirely dissolve) the aforementioned peptide ingredient and compound and, in general, a buffer can be used. Examples of the buffer which can be used include a phosphate buffer, a carbonate buffer, etc.

In addition, examples of the condensation additive which can be used for producing the polypeptide of the present invention include, in addition to N-hydroxytriazoles such as 1-hydroxybenzotriazole (HOBt), N-hydroxy polyvalent carboxylic acid imides [e.g., N-hydroxydicarboxylic acid imides such as N-hydroxysuccinimide (HONSu) and N-hydroxy-5-norbornene-2,3-dicarboxylic acid imide (HONB)], triazines such as 3-hydroxy-4-oxo-3,4-dihydro-1,2,3-benzotriazine (HOObt), and 2-hydroxyimino-2-cyanoacetic acid ethyl ester, etc. These condensation additives can be used alone or in combination of two or more thereof. N-hydroxybenzotriazoles such as 1-hydroxybenzotriazole (HOBt) are a preferable condensation additive.

An amount of the condensation additive to be used is for example about 0.5-5 mole, preferably about 0.7-2 mole, and more preferably about 0.8-1.5 mole based on 1 mole of a total amount of the reaction ingredients (1a), (2a) and (3), regardless of a kind of a solvent.

Examples of the dehydration-condensation reagent which can be used for producing the polypeptide of the present invention include, in addition to 1-ethyl-3-(3-dimethylaminopropyl)-carbodiimide hydrochloride (WSCl—HCl), carbodiimide-based condensation reagent [diisopropylcarbodiimide (DIPC), 1-ethyl-3-(3-dimethylaminopropyl)-carbodiimide (EDC=WSCl), dicyclohexylcarbodiimide (DCC), etc.], fluorophosphate-based condensation reagent [O-(7-azabenzotriazol-1-yl)-1,1,3,3-tetramethyluronium hexafluorophosphate, O-benzotriazol-1-yl-N,N,N',N'-tetramethyluronium hexafluorophosphate, benzotriazol-1-yl-oxy-tris-pyrrolidinophosphonium hexafluorophosphate, benzotriazol-1-yl-tris(dimethylamino)phosphonium hexafluorophosphide (BOP), etc.], diphenylphosphoryl azide (DPPA), etc. These dehydration-condensation reagent can be used alone or in combination of two or more thereof. A carbodiimide-based condensation reagent such as 1-ethyl-3-(3-dimethylaminopropyl)-carbodiimide hydrochloride is a preferable dehydration-condensation reagent.

An amount of the dehydration-condensation reagent to be used is, in the case where a nonaqueous solvent is used, generally about 0.7-5 moles, preferably about 0.8-2.5 moles, and more preferably about 0.9-2.3 moles (for example, 1-2 moles) based on 1 mole of a total amount of the reaction ingredients (1a), (2a) and (3). On the other hand, in the case where a solvent containing water (aqueous solvent) is used, the amount is generally about 2-500 moles (for example, 2-50 moles), preferably about 5-250 moles (for example, 5-25 moles), and more preferably about 10-125 moles (for example, 10-20 moles) based on 1 mole of a total amount of the reaction ingredients (1a), (2a) and (3), since there is inactivation of the dehydration-condensation reagent due to water.

In the condensation reaction upon producing the polypeptide of the present invention, a pH of a reaction system may be adjusted, or a base which is not involved in the reaction may be added. Adjustment of the pH can be conducted with an inorganic base [sodium hydroxide, potassium hydroxide, sodium carbonate, sodium hydrogen carbonate, etc.], an organic base, an inorganic acid [hydrochloric acid, etc.] and an organic acid, and the reaction solution is generally adjusted to in the vicinity of a neutral range (pH=about 6-8). Examples of the base which is not involved in the reaction include tertiary-amines such as trialkylamines such as trimethylamine, triethylamine and diisopropylethylamine, and heterocyclic tertiary amines such as N-methylmorpholine and pyridine. An amount of the base to be used is generally about one to two folds of a total mole of amino groups in the peptide ingredient and the compound.

In addition, in the third aspect, the present invention provides a polypeptide derivative in which a useful substance is conjugated to the polypeptide via a dicarboxylic acid linker of the polypeptide.

In addition, examples of the useful substance to be conjugated to the polypeptide to which dicarboxylic acid is added include a peptide such as an oligopeptide and a polypeptide, a protein, a nucleic acid such as a DNA and an RNA, a sugar, a polysaccharide, a lipid such as a phospholipid and a steroid, a polymer such as a polyethyleneglycol derivative, an antimicrobial agent, apatite, etc., which have various biological activities and biological functions. In addition, these useful substances can be conjugated to the polypeptide of the present invention alone or as a complex of two or more thereof.

Examples of the useful substance to be conjugated to the polypeptide include a biologically-active peptide such as a peptide having partly or entirely a sequence Tyr-Arg-His-Ala-Trp-Ser-Glu-Asn-Leu-Ala-Gln-Cys-Phe-Asn (SEQ ID NO:1) which has apoptosis-suppressing action and neural stem cell differentiation promoting action, a peptide having partly or entirely a sequence Lys-Ile-Pro-Lys-Ala-Ser-Ser-Val-Pro-Thr-Glu-Leu-Ser-Ala-Ile-Ser-Thr-Leu-Tyr-Leu (SEQ ID NO:2) which has osteogenic action, a peptide having partly or entirely a sequence Gly-Arg-Gly-Asp-Ser (SEQ ID NO:3) which has a cell adhesion activity; a protein such as basic fibroblast growth factor (bFGF) having skin cell growth action and vascularization action; a nucleic acid such as RNA having gene expression-suppressing action such as a short interference RNA (siRNA), a short hairpin RNA (shRNA), a cDNA/RNAi hybrid molecule, or a plasmid DNA encoding the green fluorescence protein; a sugar or a polysaccharide such as cyclodextrin having drug clathrate action; a lipid such as a phospholipid such as phosphatidylethanolamine or a steroid such as estrogen and progesterone; a polymer such as a polyethyleneglycol derivative such as PEG 400 amine and PEG 1500 amine; an antimicrobial agent such as gentamycin, penicillin and ofloxacin; and apatite such as hydroxy-apatite, etc.

The useful substance is conjugated to a hydroxyproline (Hyp) residue of the polypeptide via the dicarboxylic acid linker. In general, the useful substance is conjugated to the dicarboxylic acid linker of the polypeptide of the present invention via a covalent bond, but it depends on a kind or a nature of the useful substance. In the case where apatite is conjugated to the polypeptide, it is conjugated via an ionic bond due to its nature. Apatite can be carried by the polypeptide of the present invention or the polypeptide derivative to which the useful substance is conjugated. Apatite can be carried by the polypeptide or polypeptide derivative by contacting the polypeptide or polypeptide derivative with an aqueous solution containing calcium and phosphoric acid ions to deposit apatite on the polypeptide or polypeptide derivative.

In addition, a conjugation ratio of the useful substance to the hydroxyproline residue of the polypeptide of the present invention is preferably 1/100-100/100, more preferably 5/100-90/100, and most preferably 10/100-80/100. The ratio less than 1/100 is not preferable since an added amount of the useful substance is small and it becomes difficult to adequately exert an objective effect. On the other hand, when the ratio is 100/100, a structure is such that the useful substance is conjugated to all of the hydroxyproline residues of the polypeptide, and the ratio does not go beyond it.

The molecular weight of the polypeptide or polypeptide derivative of the present invention can be measured, for example, by gel permeation chromatography.

The polypeptide or polypeptide derivative of the present invention preferably has infrared spectrum absorption at 1700-1800 cm$^{-1}$. When there is no infrared spectrum absorption peak within this range, an amount of the dicarboxylic acid linker relative to a polypeptide chain is small and an adequate amount of the dicarboxylic acid linker cannot be conjugated to the polypeptide. Infrared spectrum absorption can be measured by FT-IR (KBr method).

An amount of the dicarboxylic acid linker conjugated to the polypeptide or polypeptide derivative of the present invention can be measured, for example, from a peak intensity ratio of an ester group and an amide group in infrared spectrum absorption. In addition, more particularly, an amount of the dicarboxylic acid linker added to the polypeptide or polypeptide derivative can be measured by quantifying an amount of unreacted dicarboxylic acid (mole number) by High Performance Liquid Chromatography after the addition reaction of dicarboxylic acid. That is, an amount of dicarboxylic acid conjugated is calculated by subtracting an amount of unreacted dicarboxylic acid from a total amount of dicarboxylic acid used for the synthesis.

An amount of the useful substance added to the polypeptide derivative of the present invention can be measured, for example, by quantifying an amount of the unreacted useful substance (mole number) by HPLC after the peptide addition reaction. That is, an amount of the useful substance conjugated can be calculated by subtracting an amount of the unreacted useful substance from a total amount of the useful substance used for the synthesis.

The polypeptide or polypeptide derivative of the present invention can form a collagen tissue, and does not cause a side effect. In addition, there is no risk of infection or propagation of a pathogen or a pathogenic factor (e.g., a protein which has converted to pathogenic one (e.g., abnormal prion, etc.), etc.) in the polypeptide or polypeptide derivative of the present invention. Thus, the polypeptide or polypeptide derivative of the present invention is highly safe. In addition, the polypeptide or polypeptide derivative is excellent in cytophilicity and biocompatibility, and action of promoting cell adhesion to a substrate such as a glass. Therefore, the polypeptide or polypeptide derivative of the present invention is useful as a biomaterial or a biocompatible material, for example, as artificial collagen, etc. In addition, the polypeptide or polypeptide derivative of the present invention can be applied to a tissue of a subject (e.g., an epidermal tissue and an dermal tissue). Examples of the subject include a human and a non-human animal (e.g., monkey, sheep, cow, horse, dog, cat, rabbit, rat, mouse, etc.).

In addition, the polypeptide or polypeptide derivative of the present invention can be used for suppressing or preventing infection or propagation which is caused from the polypeptide (e.g., infection or propagation of a pathogen or a pathogenic factor existing in the polypeptide). Therefore, the polypeptide or polypeptide derivative of the present invention can be effectively utilized, for example, at an affected part [e.g., a diseased part or a damaged part (e.g., damaged part such as scratch, burn), etc.] or a dissected part [e.g., a dissected part by surgery, etc.].

In addition, the polypeptide or polypeptide derivative of the present invention may be utilized, for example, as a medical material such as a carrier or a support for tissue engineering, a carrier or a support for regenerative medicine (artificial skin, etc.), a tissue adhesive or an adhesion-preventive biomaterial, a surgical suture, a hemostatic material, and a contact lens, a raw material (or a base) of a pharmaceutical, a raw material (or a base) of a cosmetic, or a food additive, etc.

The polypeptide or polypeptide derivative of the present invention can be configured depending on various uses according to the known methods. Thus, an application form of the polypeptide or polypeptide derivative may be liquid (a solution, a suspension, etc.), granular, two-dimensional (a film, a sheet, etc.) or three-dimensional. For example, a film or a sheet of the polypeptide or polypeptide derivative can be prepared by casting a solution or suspension of the polypeptide or polypeptide derivative on a peelable base (e.g., fluorine resin (polytetrafluoroethylene) sheet) and drying it.

In addition, a fiber of the polypeptide or polypeptide derivative can be prepared by extruding through a nozzle a solution or suspension of the polypeptide or polypeptide derivative into a solution containing a salt of a high concentration or a solvent which does not dissolve the polypeptide.

In addition, a gel of the polypeptide or polypeptide derivative can be prepared by standing an aqueous solution or suspension of the polypeptide or polypeptide derivative, or if necessary, by adding a polyvalent cross-linker (glutaraldehyde, etc.) to the solution or the suspension and standing it.

Furthermore, the polypeptide or polypeptide derivative can be prepared as a spongiose porous product by lyophilizing the gel prepared. In addition, the porous product can be also prepared by stirring and bubbling the solution or suspension of the polypeptide or polypeptide derivative and drying it.

Furthermore, the polypeptide or polypeptide derivative of the present invention can be utilized as a coating agent. For example, a surface of a base can be coated with the polypeptide of the present invention by applying or spraying the solution or suspension of the polypeptide on the surface of the base and drying it. Such the base may be a molded product which is made of various materials such as a metal, ceramics, a plastic, a natural polymer and glass, and a shape of the molded product may be granular, linear or fibrous, a two-dimensional structure such as a film or a sheet, or a three-dimensional structure. In addition, the polypeptide may be sustained in a porous product by impregnating the porous product (a two-dimensional porous product such as a granular porous product, cellulosic paper, nonwoven fabric or woven fabric, and a three-dimensional porous product such as a cylindrical product) with the solution or suspension of the polypeptide.

In the case where the polypeptide of the present invention is used as medical use, it is preferably used after disinfection or sterilization. As a method for disinfection or sterilization, various disinfection or sterilization methods such as autoclaving, gamma-ray sterilization, ethylene oxide gas sterilization, chemical disinfection, and ultraviolet-ray disinfection are used. Among them, gamma-ray sterilization and ethylene oxide gas sterilization are preferable, since they have high sterilization efficiency and have little influence on the material.

EXAMPLES

Then, the present invention will be illustrated in more detail by way of Examples, but they are intended merely as an illustration and not a limitation upon the scope of the present invention.

Example 1

In 2 mL of 10 mM phosphate buffer (pH7.4), was dissolved 100 mg (0.35 mmol) of H-Pro-Hyp-Gly-OH (Peptide Institute Inc.). To the mixture, was added 9.5 mg (0.07 mmol) of 1-hydroxybenzotriazole and it was dissolved with stirring. The mixture was cooled at 4 C°, 335 mg (1.75 mmol) of 1-ethyl-3-(3-dimethylaminopropyl)carbodiimide hydrochloride (EDC HCl) was added while stirring, and stirring was continued at 4° C. for 2 hours. Then, the reaction solution prepared by stirring at 20° C. for 2 days was diluted with 4 mL of 10 mM phosphate-buffered saline (containing 0.15M NaCl, pH 7.4), and was dialyzed for 3 days against milliQ water to remove a reagent such as a condensation reagent and an unreacted monomer.

The resulting polypeptide was applied to gel permeation chromatography (Amersham Biosciences Inc., AKTApurifier system, column: Superdex 200 HR GL, flow rate: 0.5 mL/min., eluent: 10 mM phosphate-buffered saline (containing 0.15M NaCl, pH7.4), and a peak of the polypeptide was observed at an elution position above the molecular weight of 100,000. The molecular weight of the polypeptide was calculated with polyethyleneglycol standards (Fluka).

In addition, when circular dichroism spectrum of the resulting polypeptide was measured, positive and negative Cotton effects of the polypeptide were observed at 225 nm and 197 nm, respectively. This confirmed that the polypeptide forms a triple helix structure.

Then, an aqueous solution of the resulting polypeptide was lyophilized to prepare a spongiose polypeptide. This polypeptide (10 mg) was cut into about 1 mm square cube and it was washed twice with a small amount of dimethylformamide (DMF). To the sponge washed, was added 37 mg (0.37 mmol) of succinic anhydride (Wako Pure Chemical Industries, Ltd., special grade reagent) which had been purified by recrystallization from hot isopropanol and 64 µL (0.37 mmol) of diisopropylethylamine (DIPEA) under ice-cooling, and the mixture was stirred overnight at room temperature. The resulting reaction solution was diluted about 5-folds with milliQ water and it was dialyzed against milliQ water for 2 days to remove the unreacted reagent.

The infrared spectrum measurement of the resulting succinylated polypeptide revealed absorption of an ester at 1735 $cm^{-1}$ and, thereby, addition of a succinic acid linker to the polypeptide chain was confirmed. In addition, from an intensity ratio relative to amide absorption at 1639 $cm^{-1}$, it was found that a ratio of peptide units (1) and (2)((1)/(2)) is 31/69 (molar ratio). In addition, when the circular dichroism spectrum of the resulting succinylated polypeptide was measured in an aqueous solution at 20° C., positive and negative Cotton effects were observed at 225 nm and 199 nm, respectively. This confirmed that the polypeptide forms a triple helix structure.

The resulting succinylated polypeptide was lyophilized, and 5 mg of which was washed once with dimethylformamide (DMF). To this, 21 mg (0.185 mmol) of N-hydroxysuccinimide and 35 mg (0.185 mmol) of 1-ethyl-3-(3-dimethylaminopropyl)-carbodiimide hydrochloride were added and the mixture was stirred overnight at room temperature. Then, the reaction product was washed five times with dimethylformamide (DMF), and 3.2 mg (0.00185 mmol) of the peptide: Tyr-Arg-His-Ala-Trp-Ser-Glu-Asn-Leu-Ala-Gln-Cys-Phe-Asn-NH$_2$ (SEQ ID NO:1)(Peptide Institute, Inc.) dissolved in 200 µL of dimethylformamide (DMF) was added thereto. Further, 3.2 µL (0.0185 mmol) of diisopropylethylamine was added under ice-cooling, and the mixture was stirred overnight at room temperature. The reaction product was washed once with dimethylformamide (DMF) and then twice with methanol, and it was dried under reduced pressure. A conjugation ratio of the peptide to the polypeptide chain was found to be 0.4 mg/mg from a peptide concentration in a supernatant before and after the reaction, which was measured by HPLC (column: Waters NovaPak C18 3.9×150 mm column, eluent: 0.05% TFA-acetonitrile in water, linear gradient (5%-50%/30 min.), flow rate 1 ml/min., detection wavelength 215 nm).

Experimental Example 1

The polypeptide prepared in Example 1 (succinylated polypeptide to which no peptide was conjugated) and a polypeptide derivative to which the peptide: Tyr-Arg-His-Ala-Trp-Ser-Glu-Asn-Leu-Ala-Gln-Cys-Phe-Asn-NH$_2$ (SEQ ID NO:1) was conjugated (peptide-conjugated polypeptide) were immersed in ethanol to sterilize. The peptide of SEQ ID NO:1 has apoptosis-suppressing action and neural stem cell differentiation promoting action. A neurosphere of the neural stem cell which had been isolated from brain hippocampus of a 16-days old fetal Wistar rat was co-cultured with a sterilized polypeptide or polypeptide derivative for 5 days in a D-MEM/F12 medium containing 1% of N-2 supplement and 20 ng/mL of bFGF. As the result, the neurosphere adhered on the peptide-conjugated polypeptide, and extended a neurite. To the contrary, the neurosphere did not adhere on the succinylated polypeptide to which no peptide was conjugated, and no extension of a neurite was observed. That is, it was found that the peptide-conjugated polypeptide promotes neural differentiation of the neural stem cell.

Example 2

A spongiose polypeptide was prepared by lyophilizing an aqueous solution of a polypeptide which was prepared from the peptide unit, H-Pro-Hyp-Gly-OH according to a similar procedure to that of Example 1. This polypeptide (10 mg) was cut into about 1 mm square cube and it was washed twice with a small amount of dimethylformamide (DMF). To the polypeptide washed, were added 3.7 mg (0.037 mmol) of succinic anhydride (Wako Pure Chemical Industries, Ltd., special grade reagent) which had been purified by recrystallization from hot isopropanol and 6.4 µL (0.037 mmol) of diisopropylethylamine (DIPEA) under ice-cooling, followed by stirring overnight at room temperature. Methanol was added to the resulting reaction solution, and it was washed five times with methanol to remove the unreacted reagent.

The infrared spectrum measurement of the resulting succinylated polypeptide revealed absorption of an ester at 1735 $cm^{-1}$. This confirmed addition of succinic acid to the polypeptide chain. In addition, from an intensity ratio relative to amide absorption at 1640 $cm^{-1}$, it was found that a ratio of peptide units (1) and (2) ((1)/(2)) is 62/38 (molar ratio).

The circular dichroism spectrum measurement of the resulting succinylated polypeptide revealed positive and negative Cotton effects at 224 nm and 199 nm, respectively. This confirmed that the polypeptide forms a triple helix structure.

About 5 mg of the resulting polypeptide was allowed to stand overnight in a 1M aqueous solution of $CaCl_2$ at room temperature. The polypeptide was washed twice with milliQ water, and was immersed in an aqueous solution containing $Na^+$ 213 mM, $K^+$ 7.5 mM, $Ca^{2+}$ 3.8 mM, $Mg^{2+}$ 2.3 mM, $Cl^-$ 223.3 mM, $HCO^{3-}$ 6.3 mM, $HPO_4^{2-}$ 1.5 mM and $SO_4^{2-}$ 0.75 mM which had been adjusted to pH 7.25 with a Tris buffer, followed by allowing to stand at 37° C. for 7 days. Then, the polypeptide was washed twice with milliQ water and three times with methanol, and was dried under reduced pressure. When a surface of the polypeptide after drying was deposited with gold and observed with a scanning electron microscope (Hitachi Co. Ltd., Model S-4800N), an apatite crystal was observed on a surface of the polypeptide.

Example 3

In 2 mL of 10 mM phosphate buffer (PB, pH7.4), was dissolved 100 mg (0.35 mmol) of Pro-Hyp-Gly (Peptide Institute Inc.) with stirring. To this solution, was added 9.5 mg (0.07 mmol) of 1-hydroxybenzotriazole (HOBt), and the mixture was stirred to dissolve the materials. After dissolution, the solution was cooled to 4° C., 201 mg (1.05 mmol) of 1-ethyl-3-(3-dimethylaminopropyl)-carbodiimide hydrochloride (EDC HCl) was added thereto with stirring, and stirring was further continued at 4° C. for 90 minutes.

To the solution, was added 4 mL of 10 mM phosphate-buffered saline (PBS, pH 7.4), and the mixture was vigorously stirred and then dialyzed against milliQ water for 2 days. When the resulting polypeptide was applied to gel permeation chromatography (Amersham Biosciences, AKTA-purifier system, column: Superdex 200 HR GL, flow rate: 0.5 mL/min, eluent: PBS), a peak of the polypeptide was observed at an elution position above the molecular weight of 100,000 (7.25 mL). The molecular weight of the polypeptide was calculated with polyethyleneglycol standards (Fluka).

In addition, when circular dichroism spectrum of the resulting polypeptide was measured, positive and negative Cotton effects were observed at 225 nm and 197 nm, respectively. This confirmed that the polypeptide forms a triple helix structure.

Then, 0.1% aqueous solution of the resulting poly(Pro-Hyp-Gly)(1.0 mL) was added to a glass petri dish having an inner diameter of 28 mm and it was allowed to stand for 60 hours in a desiccator to prepare a film. The resulting film was washed twice with a small amount of dimethylformamide (DMF). After washing, 3.7 mg (0.037 mmol) of succinic anhydride which had been purified by recrystallization from hot isopropanol and 6.4 μL (0.037 mmol) of diisopropylethylamine (DIPEA) were added to the film under ice-cooling and the mixture was shaken overnight at room temperature. The film was washed twice with dimethylformamide (DMF) and five times with methanol, and was dried under reduced pressure.

When a part of the resulting film was collected and its infrared spectrum was measured according to a KBr method, an absorption peak was observed at 1731 $cm^{-1}$, which attributes to an ester bond. This confirmed progression of a succination reaction.

The resulting succinylated poly(Pro-Hyp-Gly) film was washed once with dimethylformamide (DMF), and 4.3 mg (0.037 mmol) of N-hydroxysuccinimide and 7.1 mg (0.037 mmol) of 1-ethyl-3-(3-dimethylaminopropyl)-carbodiimide hydrochloride (EDC HCl) were added thereto, and the mixture was shaken overnight at room temperature. After washing five times with dimethylformamide (DMF), 0.18 mg (0.37 mmol) of Gly-Arg-Gly-Asp-Ser (SEQ ID NO: 3) (Peptide Institute Inc.) and 0.048 mg (0.37 mop of diisopropylethylamine (DIPEA) were added thereto, and the mixture was shaken overnight at room temperature. The film was washed twice with dimethylformamide (DMF) and five times with methanol, and was sterilized by immersing three times in ethanol with shaking.

A NIH3T3 cell suspended in D-MEM was added onto the resulting Gly-Arg-Gly-Asp-Ser-conjugated poly(Pro-Hyp-Gly) film at a ratio of $10^4$ cells/$cm^2$, followed by allowing to stand in 5% $CO_2$ at 37° C. for 1 hour. The non-adhered cell was washed out three times with PBS and the number of adhered cells was counted at five positions on the film.

As the result, it was found that the cells were adhered on the Gly-Arg-Gly-Asp-Ser-conjugated poly(Pro-Hyp-Gly) film at 7,900 cells/$cm^2$ on average, whereas, the cells were adhered on the poly(Pro-Hyp-Gly) film to which no Gly-Arg-Gly-Asp-Ser is conjugated at 2,000 cells/$cm^2$ on average, on a plastic dish coated with bovine collagen type I at 6,000 cells/$cm^2$ on average, and on a non-coated plastic dish at 4,500 cells/$cm^2$ on average. This demonstrated that the Gly-Arg-Gly-Asp-Ser-conjugated poly(Pro-Hyp-Gly) film has excellent cell adhesion promoting action.

INDUSTRIAL APPLICABILITY

The polypeptide or polypeptide derivative of the present invention can be utilized as a medical material such as a carrier or support for tissue engineering or regenerative medicine (an artificial skin, etc.), a tissue adhesive or an adhesion-preventive biomaterial, a surgical suture, a hemostatic material and a contact lens, a base material (or a base) for a medicine or a cosmetic, and a food additive, etc., in medical, pharmaceutical, cosmetic and food fields.

Sequence Listing Free Text
SEQ ID NO: 1
Peptide showing both inhibition of apoptosis and promotion of neuronal differentiation of neuronal stem cells.
SEQ ID NO: 2
Peptide having osteogenic action.
SEQ ID NO: 3
Peptide showing cell adhesion action.

What is claimed is:

1. A polypeptide comprising a peptide unit having an amino acid sequence represented by the formula:

-Pro-X-Gly-    (1)

wherein X represents Pro or Hyp and a peptide unit having an amino acid sequence represented by the formula:

-Pro-Hyp(O—Y—Z)-Gly-    (2)

wherein Y represents a carbonyl group, a saturated or unsaturated hydrocarbon group with or without a carbonyl group, or a saturated or unsaturated hydrocarbon group with or without a carbonyl group, including an aromatic group, and Z represents a carboxyl group.

2. The polypeptide according to claim 1, wherein Y is one or more groups selected from the group consisting of —(C=O)—$(CH_2)_n$— wherein n represents an integer of 0 or 1-18; —(C=O)—$(CH_2)_n$—(CH=CH)$_m$—$(CH_2)_k$— wherein n and k represent independently an integer of 0 or 1-18, and m represents an integer of 1-18; and —(C=O)—$(CH_2)_n$—$(C_6H_4)$—$(CH_2)_k$— wherein n and k represent independently an integer of 0 or 1-18, and $C_6H_4$ represents a phenylene group.

3. The polypeptide according to claim 1, wherein a ratio between said polypeptide unit (1) and said polypeptide unit (2) ((1)/(2)) is 99.9/0.1-1/99 in terms of a molar ratio.

4. The polypeptide according to claim 1, which exhibits a positive Cotton effect at a wavelength of 220-230 nm and a negative Cotton effect at a wavelength of 195-205 nm in circular dichroism spectroscopy.

5. The polypeptide according to claim 4, wherein at least a part of the polypeptide forms a triple helix structure.

6. The polypeptide according to claim 1, which has a peak in a molecular weight range of $5 \times 10^3$-$5 \times 10^6$.

7. The polypeptide according to claim 1, which can form a collagen tissue.

8. A polypeptide derivative, in which one or more substances selected from the group consisting of a peptide, a protein, a polypeptide, a nucleic acid, a sugar, a polysaccharide, a lipid, a polyethylene glycol derivative, an antimicrobial agent, apatite and a complex thereof are conjugated to the polypeptide as defined in claim 1.

9. A polypeptide derivative, in which the substances as defined in claim 8 are conjugated to a Hyp residue of the polypeptide via a dicarboxylic acid linker of the polypeptide.

10. A polypeptide derivative, in which apatite forms a complex with the polypeptide as defined in claim 1 or polypeptide derivative as defined in claim 8.

11. A process for producing the polypeptide as defined in claim 1, comprising reacting a compound represented by the formula:

HO—Y—Z (3)

or an anhydride thereof,
wherein Y represents a carbonyl group, a saturated or unsaturated hydrocarbon group with or without a carbonyl group, or a saturated or unsaturated hydrocarbon group with or without a carbonyl group, including an aromatic group, and Z represents a carboxyl group, with a polypeptide prepared by condensing a peptide unit having an amino acid sequence represented by the formula:

H-(Pro-Pro-Gly)$_o$-OH (1a)

wherein o represents an integer of 1 or more, and a peptide unit having an amino acid sequence represented by the formula:

H(-Pro-Hyp-Gly-)$_p$-OH (2a)

wherein p represents an integer of 1 or more.

12. A process for producing a polypeptide derivative, further comprising reacting one or more substances selected from the group consisting of a peptide, a protein, a polypeptide, a nucleic acid, a sugar, a polysaccharide, a lipid, a polyethylene glycol derivative, an antibacterial agent, apatite and a complex thereof with the polypeptide produced in the process as defined in claim 11.

13. A process for producing a polypeptide derivative, further comprising conjugating one or more of said substances to a Hyp residue of the polypeptide via a carboxylic acid linker of the polypeptide produced in the process as defined in claim 12.

14. A process for producing a polypeptide derivative forming a complex with apatite, comprising contacting the polypeptide as defined in claim 1 or polypeptide derivative as defined in claim 8 with an aqueous solution containing calcium and phosphoric acid ions to deposit apatite on the polypeptide or polypeptide derivative.

15. The process according to claim 14, wherein said apatite is hydroxy-apatite.

16. A polypeptide derivative forming a complex with apatite, prepared by the process as defined in claim 14.

17. A polypeptide derivative comprising a peptide unit having an amino acid sequence represented by the formula:

-Pro-Hyp-Gly- (1b)

and a peptide unit having an amino acid sequence represented by the formula:

-Pro-Hyp(O—CO—(CH$_2$)$_2$—CO-AA)-Gly- (2b)

wherein AA represents OH or Tyr-Arg-His-Ala-Trp-Ser-Glu-Asn-Leu-Ala-Gln-Cys-Phe-Asn-NH$_2$ (SEQ ID NO: 1).

* * * * *